(12) United States Patent
Matsuura

(10) Patent No.: US 10,471,191 B2
(45) Date of Patent: Nov. 12, 2019

(54) BLOOD TREATMENT FILTER AND BLOOD TREATMENT FILTER MANUFACTURING METHOD

(71) Applicant: ASAHI KASEI MEDICAL CO., LTD., Tokyo (JP)

(72) Inventor: Yoshimasa Matsuura, Tokyo (JP)

(73) Assignee: ASAHI KASEI MEDICAL CO., LTD., Tokyo (JP)

(*) Notice: Subject to any disclaimer, the term of this patent is extended or adjusted under 35 U.S.C. 154(b) by 121 days.

(21) Appl. No.: 15/318,109

(22) PCT Filed: Jul. 6, 2015

(86) PCT No.: PCT/JP2015/069418
§ 371 (c)(1),
(2) Date: Dec. 12, 2016

(87) PCT Pub. No.: WO2016/006575
PCT Pub. Date: Jan. 14, 2016

(65) Prior Publication Data
US 2017/0119941 A1 May 4, 2017

(30) Foreign Application Priority Data

Jul. 7, 2014 (JP) .................................. 2014-139888
Jul. 7, 2014 (JP) .................................. 2014-139889

(51) Int. Cl.
*A61M 1/02* (2006.01)
*A61M 1/34* (2006.01)
(Continued)

(52) U.S. Cl.
CPC ............ *A61M 1/0218* (2014.02); *A61M 1/02* (2013.01); *A61M 1/34* (2013.01); *A61M 1/3403* (2014.02);
(Continued)

(58) Field of Classification Search
None
See application file for complete search history.

(56) References Cited

U.S. PATENT DOCUMENTS 4,157,967 A 6/1979 Meyst et al.
5,723,047 A 3/1998 Turnbull
(Continued)

FOREIGN PATENT DOCUMENTS

CN 101282750 10/2008
CN 101646469 2/2010
(Continued)

OTHER PUBLICATIONS

Search Report issued in European Patent Office (EPO) Patent Application No. 15819032.2, dated May 17, 2017.
(Continued)

*Primary Examiner* — Benjamin M Kurtz
(74) *Attorney, Agent, or Firm* — Greenblum & Bernstein, P.L.C.

(57) ABSTRACT

A blood processing filter for removing undesirable components from liquid containing a blood component or blood, comprises a sheet-shaped filter element, and a container that includes an inlet-side container element and an outlet-side container element that are disposed to clamp the filter element, and has an internal space separated by the filter element into an inlet space and an outlet space. The filter element includes a pair of filtering surfaces disposed on the inlet space side and the outlet space side, and an end surface along a periphery of the pair of the filtering surfaces, and the inlet-side container element and the outlet-side container element are provided with a gripper that clamps and compresses outer edge portions of the pair of filtering surfaces,
(Continued)

and adheres to the end surface with melt resin, and a part of the container is provided with a steam-permeable portion having steam permeability.

9 Claims, 13 Drawing Sheets

(51) Int. Cl.
*B01D 29/00* (2006.01)
*B01D 35/18* (2006.01)
*B29C 65/70* (2006.01)
*B29D 22/00* (2006.01)
*B29C 45/00* (2006.01)
*A61M 1/36* (2006.01)
*B29L 31/14* (2006.01)
*B29L 31/00* (2006.01)

(52) U.S. Cl.
CPC ........... *A61M 1/36* (2013.01); *B01D 29/0093* (2013.01); *B01D 29/0095* (2013.01); *B01D 35/18* (2013.01); *B29C 45/006* (2013.01); *B29C 65/70* (2013.01); *B29D 22/00* (2013.01); A61M 2207/00 (2013.01); B29C 2045/0067 (2013.01); B29L 2031/14 (2013.01); B29L 2031/753 (2013.01)

(56) References Cited

U.S. PATENT DOCUMENTS

| | | | |
|---|---|---|---|
| 6,168,718 | B1 | 1/2001 | Sutter et al. |
| 2005/0005680 | A1 | 1/2005 | Anderson |
| 2005/0056580 | A1* | 3/2005 | Reitz ................... A61M 1/3633 210/232 |
| 2006/0049097 | A1 | 3/2006 | Cavallini et al. |
| 2006/0108272 | A1 | 5/2006 | Ariagno et al. |
| 2009/0045131 | A1 | 2/2009 | Omori et al. |
| 2010/0084326 | A1 | 4/2010 | Takesawa |
| 2011/0240549 | A1* | 10/2011 | Andou ................ A61M 1/3636 210/435 |
| 2016/0243293 | A1 | 8/2016 | Matsuura |

FOREIGN PATENT DOCUMENTS

| | | |
|---|---|---|
| CN | 202554574 | 11/2012 |
| CN | 102821795 | 12/2012 |
| CN | 105592869 | 5/2016 |
| EP | 0526678 | 2/1993 |
| EP | 3053612 | 8/2016 |
| JP | 52-116969 | 9/1977 |
| JP | 7-267871 | 10/1995 |
| JP | 9-168703 | 6/1997 |
| JP | 11-216179 | 8/1999 |
| JP | 2001-226271 | 8/2001 |
| JP | 2007-504947 | 3/2007 |
| JP | 2007-97746 | 4/2007 |
| JP | 2011-72814 | 12/2010 |
| JP | 2011-72816 | 4/2011 |
| JP | 2011-255043 | 12/2011 |
| JP | 2012-139347 | 7/2012 |
| JP | 6101356 | 3/2017 |
| WO | 95/017236 | 6/1995 |
| WO | 2004/050147 | 6/2004 |
| WO | 2011/122564 | 10/2011 |
| WO | 2015/050213 | 4/2015 |
| WO | 2015/050215 | 4/2015 |

OTHER PUBLICATIONS

Search Report issued in Japan Patent Application No. PCT/JP2015/069418, dated Oct. 6, 2015.
International Preliminary Report on Patentability issued in Japan Patent Application No. PCT/JP2015/069418 and English translation thereof, dated Jan. 19, 2017.

* cited by examiner

BLOOD TREATMENT FILTER AND BLOOD TREATMENT FILTER MANUFACTURING METHOD

TECHNICAL FIELD

The present invention relates to a blood processing filter for removing undesirable components, such as aggregates and leukocytes, from liquid containing blood components or blood, and to a blood processing filter manufacturing method. In particular, the blood processing filter is, for example, a disposable blood processing filter, and is used for the sake of removing microaggregates and leukocytes which may cause side effects from whole blood preparations, erythrocyte preparations, thrombocyte preparations, blood plasma preparations and the like for blood transfusion.

BACKGROUND ART

It is becoming common for whole blood collected from a donor to be separated into blood component preparations, such as an erythrocyte preparation, a thrombocyte preparation, and a blood plasma preparation, stored and then provided for transfusion. Since microaggregates and leukocytes included in these blood preparations cause various side effects of blood transfusion, many methods of removing these undesirable components before transfusion and then performing transfusion, or of removing these undesirable components after blood collection, temporarily storing the preparations, and then providing the preparations for transfusion have been widely used.

Among methods of removing these undesirable components from blood preparations, processing blood preparations through a blood processing filter is most typical. Two types of blood processing filters are used; one is what includes a filter element made of nonwoven fabric or a porous body equipped in, for example, a flexible container as described in Patent Literatures 1 to 5, and the other is what includes the filter element equipped in a hard container made of polycarbonate or the like.

Typically, for processing of a blood preparation through a blood processing filter, a blood preparation bag containing the blood preparation to be processed is connected to an inlet of the blood processing filter, the blood preparation bag is placed at a position higher than the blood processing filter by approximately 20 to 100 cm. As a result, the blood preparation is introduced from the blood preparation bag into the blood processing filter by the action of gravity. Meanwhile, a recovery bag for accommodating the filtered blood preparation is connected to an outlet of the blood processing filter. The recovery bag is placed at a lower position by approximately 50 to 100 cm than that of the blood processing filter. As a result, the filtered blood preparation is collected in the recovery bag by the action of gravity. At this time, a pressure loss occurs due to the resistance of the filter element, in an inlet-side space in the blood processing filter container with respect to the filter element, whereby the space becomes a positive pressure. On the contrary, in an outlet-side space with respect to the filter element, the blood preparation flows from the outlet, whereby the space becomes a negative pressure.

Since a blood processing filter with a flexible container as shown in Patent Literatures 1 to 5 has a container that is flexible, the container swells like a balloon due to a positive pressure in an inlet-side space, and the filter element is pressed against on the outlet side of the container. On the other hand, in an outlet-side space, the container is in close contact with the filter element due to a negative pressure, and the state is brought into that where the opening of the outlet is blocked. That is, since blood tends to flow from the filter but the opening is blocked, it is difficult for the blood to flow out.

On the contrary, a blood processing filter with a hard container does not largely deform even during filtration, the filter element is not pressed against the outlet-side, and the state is not brought into that where the opening of the outlet is blocked. Such a hard container includes an inlet-side container element and an outlet-side container element which are fitted with each other, and rib-shaped convexes provided for the inlet-side container element and the outlet-side container element are pressed against each other, thereby clamping the outer edge portion of the filter element. By pressing the convexes against each other to a high density, the side leakage (side flow) where blood flows over the outer edge portion of the filter element without being filtered can be prevented.

Incidentally, the entire apparatus is required to be sterilized in order to be used for processing blood preparations. Typically, steam sterilization is applied. The filter for the hard container has a poor steam permeability, and is required to be subjected to a long sterilization time. However, execution of a long-time autoclave sterilization causes degradation of blood stock solution and the like. Accordingly, after the filter is sterilized in a separated manner and the blood bag, circuit and the like are then connected, sterilization is required to be performed again. Thus, complicated operations are required to be executed.

A filter described in Patent Literature 6 has been invented as means for solving this. In this filter, a part of or the entire inlet-side container element is made of a flexible member, and a part of or the entire outlet-side container element is made of a hard member. In this filter, adoption of the hard member for the outlet-side container element can prevent a poor blood flow due to close contact of the outlet-side container element with the filter element, while adoption of the flexible member for the inlet-side container element can secure steam permeability during steam sterilization.

CITATION LIST

Patent Literature

[Patent Literature 1] Japanese Unexamined Patent Publication No. H11-216179
[Patent Literature 2] Japanese Unexamined Patent Publication No. H7-267871
[Patent Literature 3] International Publication No. WO 2004/050147
[Patent Literature 4] International Publication No. WO 95/17236
[Patent Literature 5] European Unexamined Patent Publication No. 0526678
[Patent Literature 6] Japanese Unexamined Patent Publication No. 2011-072814

SUMMARY OF INVENTION

Technical Problem

However, as a result of verification by the present inventors, it has become apparent that there is a possibility that in the filter that concurrently adopts a flexible member and a hard member for parts of or the entire inlet-side container element and outlet-side container element, contraction of resin being subject to steam at high temperature and high pressure affects attachment of the inlet-side container element, the filter element, and the outlet-side container element, reduces the performance of removing undesirable components, and breakage in container occurs.

The present invention has an object to solve the above problems, and thus has an object to provide a blood processing filter that can easily avoid the risk of incomplete removal of undesirable components without reducing the blood processing efficiency and is suitable for autoclave sterilization, and to provide a blood processing filter manufacturing method.

Solution to Problem

As a result of diligent research by the present inventors to solve the above problems, the inventors have found that the risk of incomplete removal of undesirable components can be easily avoided without reducing the blood processing efficiency by causing the inlet-side container element and the outlet-side container element to clamp and compress the outer edge portions of the front and back filtering surfaces of the filter element, and by bonding the end surface that is the periphery of the filter element with melt resin. Furthermore, the inventors have found knowledge that the autoclave sterilization can be improved by providing a steam-permeable portion that has steam permeability for a part of the inlet-side container element and the outlet-side container element, and thus reached an aspect of the present invention.

That is, an aspect of the present invention is a blood processing filter for removing undesirable components from liquid containing a blood component or blood, the filter comprising: a sheet-shaped filter element; and a container that includes an inlet-side container element and an outlet-side container element that are disposed to clamp the filter element, and has an internal space separated by the filter element into an inlet space and an outlet space, wherein the filter element includes a pair of filtering surfaces disposed on the inlet space side and the outlet space side, and an end surface along peripheries of the pair of filtering surfaces, the inlet-side container element and the outlet-side container element are provided with a gripper that clamps and compresses outer edge portions of the pair of filtering surfaces and adheres to the end surface with melt resin, and a part of the container is provided with a steam-permeable portion having steam permeability. Note that, blood according to the present invention includes blood preparations, such as whole blood preparations, erythrocyte preparations, thrombocyte preparations and blood plasma preparations, for blood transfusion.

The container of the blood processing filter is thus provided with the steam-permeable portions having steam permeability. Consequently, sterilization in an autoclave can be easily executed. The inlet-side container element and the outlet-side container element are provided with the gripper which clamps and compresses the outer edge portions of the pair of filtering surfaces. Furthermore, the gripper is bonded to the end surface of the filter element with melt resin. As a result, the side leakage (side flow) where undesirable components flow over the outer edge portions of the filter element without being filtered can be prevented, which is advantageous to improve blood processing efficiency. In particular, the gripper is bonded to the end surface of the filter element with melt resin. Consequently, the region of the outer edge portion compressed by the gripper to exert the advantageous effect can be reduced in comparison with a case without adhesion. As a result, the range of the filter element that does not function for blood processing is reduced, which is preferable.

The above aspect may be the blood processing filter wherein the steam-permeable portion is a film that has steam permeability and is provided for at least one of the inlet-side container element and the outlet-side container element.

The above aspect may be the blood processing filter wherein the steam-permeable portion is a part of the container and is a thin-walled portion that is thinner than other portions, and the steam-permeable portion and the other portions are integrally formed.

The above aspect may be the blood processing filter wherein the steam-permeable portion has a thickness of 50 μm or more and 500 μm or less.

In the case where the filter element is not melted at the gripper according to the above aspect, the portion where the function as the filter is lost due to melting decreases, which is further advantageous in improving the blood processing efficiency.

In the above aspect, in the case where the melt resin is made of a resin identical to that of the container, adhesion between the filter element and the container is easy, which is preferable.

In the case where in the above aspect the gripper has the resin flow path which surround the end surface of the filter element and is filled with the melt resin, the filter element is loaded in the container and subsequently the resin flow path is filled with the melt resin, thereby allowing the end surface of the filter element to adhere effectively through the resin flow path.

In the above aspect, in the case where the inlet-side container element, the outlet-side container element, and the filter element adhere over the entire periphery of the gripper in a belt-shaped manner by filling the resin flow path with the melt resin, the airtightness and liquid-tightness are high, which is preferable.

The above aspect may be the blood processing filter wherein another portion that is at least one of the inlet-side container element and the outlet-side container element and is other than the steam-permeable portion has a thickness of 1 mm or more and 5 mm or less.

Furthermore, another aspect of the present invention is a blood processing filter manufacturing method, the filter being for removing undesirable components from liquid containing a blood component or blood. This blood processing filter comprises a sheet-shaped filter element, and a container that includes an inlet-side container element and an outlet-side container element that are disposed to clamp the filter element, and has an internal space separated by the filter element into an inlet space and an outlet space, wherein the filter element includes a pair of filtering surfaces disposed on the inlet space side and the outlet space side, and an end surface along a periphery of the pair of the filtering surfaces, and the inlet-side container element and the outlet-side container element are provided with a gripper that clamps and compresses outer edge portions of the pair of filtering surfaces, and adheres to the end surface with melt resin, and a part of the container includes a steam-permeable portion having steam permeability. The blood processing filter manufacturing method comprises: a container element molding step of injection-molding the inlet-side container element with one mold and injection-molding the outlet-side container element with another mold, and forming a steam-permeable portion in at least one of the inlet-side container element and the outlet-side container element; a inserting step of inserting the filter element into the inlet-side container element or the outlet-side container element; a joining step of bringing the inlet-side container element and the outlet-side container element into contact with each other in a state where the filter element is loaded, and compresses an outer edge portion of the filter element; and an adhesion step of causing the inlet-side container element, the outlet-side container element and an end surface of the filter element to adhere to each other with melt resin.

The blood processing filter manufacturing method comprises the joining step and the adhesion step. Accordingly, the inlet-side container element and the outlet-side container element can be pressed against each other with a strong power. Consequently, the filter element can be compressed to have a high density. Furthermore, in the state of being compressed to have the high density, the inlet-side container element, the outlet-side container element and an end surface of the filter element can be adhered to each other with melt resin. As a result, the blood processing filter can effectively prevent a side leakage (side flow) where undesirable components flow over the outer edge portion of the filter element without being filtered. Furthermore, at least one of the inlet-side container element and the outlet-side container element is thus provided with the steam-permeable portion. Consequently, sterilization in an autoclave can be easily executed.

The above aspect may be the blood processing filter wherein the container element molding step forms the steam-permeable portion by providing a film having steam permeability in at least one of the inlet-side container element and the outlet-side container element.

In the container element molding step of the blood processing filter manufacturing method according to the above aspect, a portion of at least one of the inlet-side container element and the outlet-side container element may be a thin-walled portion that is thinner than other portions, and the steam permeable portion may be formed by integrally forming the thin-walled portion and the other portions.

Advantageous Effects of Invention

The present invention can easily avoid the risk of incomplete removal of undesirable components without reducing the blood processing efficiency, and improve autoclave sterilization.

BRIEF DESCRIPTION OF DRAWINGS

FIG. 8(a) shows a gripper according to a first variational example. FIG. 8(b) shows a gripper according to a second variational example. FIG. 8(c) shows a gripper according to a third variational example. FIG. 8(d) shows a gripper according to a fourth variational example.

DESCRIPTION OF EMBODIMENTS

Figure 1:
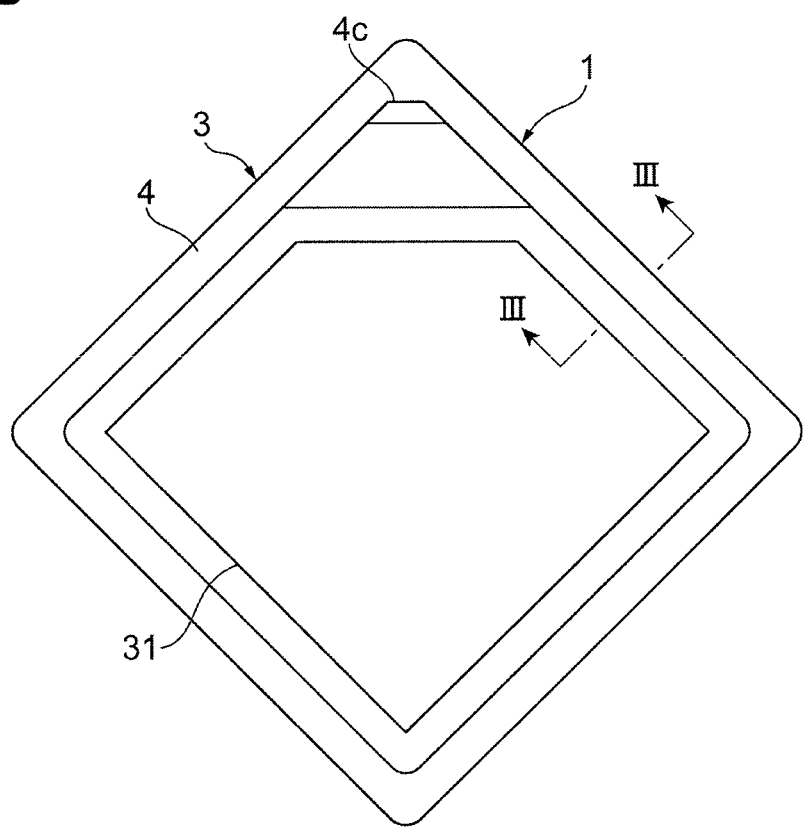
FIG. 1 is a plan view of a blood processing filter in view from the inlet-side container element according to a first embodiment of the present invention.

Hereinafter, referring to the drawings, preferred embodiments of a blood processing filter and a manufacturing the blood processing filter according to the present invention are described in detail.

First, blood processing filters 1 and 1A according to embodiments of the present invention are described referring to FIGS. 1 to 7. The blood processing filters 1 and 1A are for removing undesirable components from liquid containing blood components or blood (hereinafter, referred to as liquid to be processed). In the following description, the blood processing filter 1 according to the first embodiment is mainly described. However, the blood processing filter 1A according to the second embodiment is basically identical to the blood processing filter 1 according to the first embodiment except the steam-permeable portion of the container. Consequently, referring to FIGS. 5, 6 and 7, supplementary description of the blood processing filter 1A is made mainly on the difference from the blood processing filter 1 according to the first embodiment.

Figure 2:
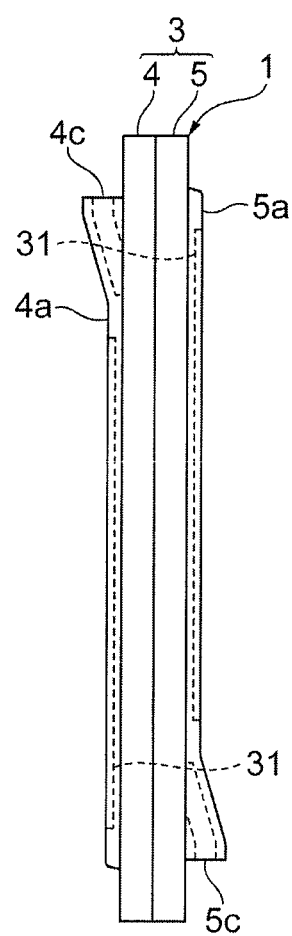
FIG. 2 is a side view of the blood processing filter according to the first embodiment of the present invention.
Figure 3:
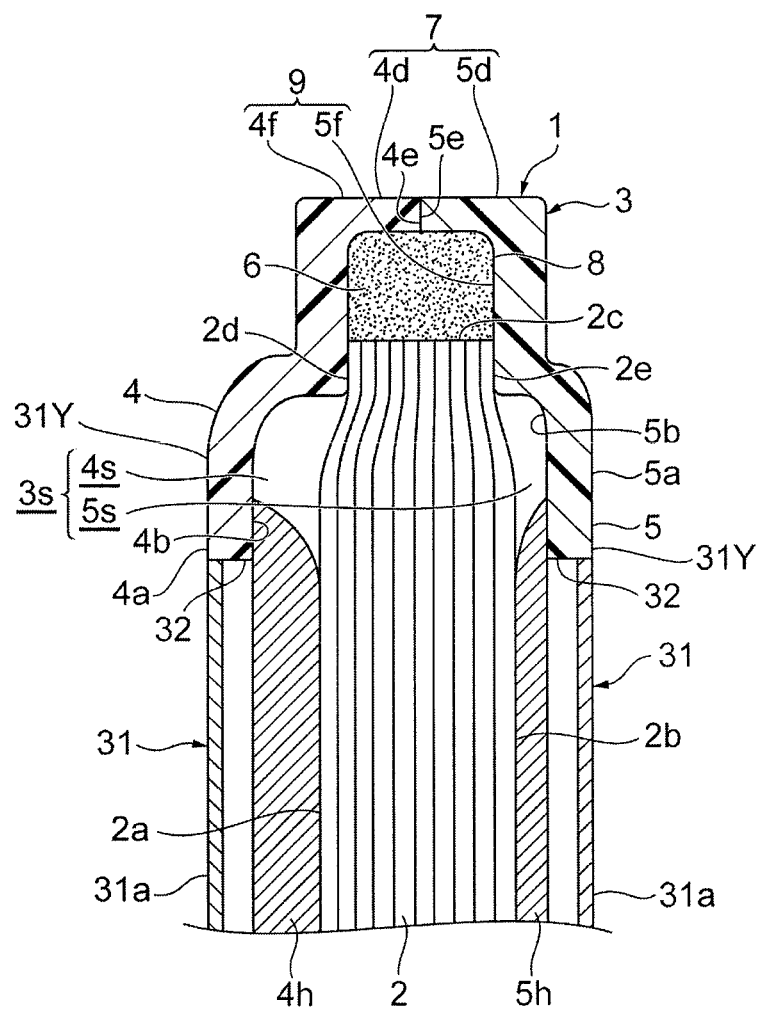
FIG. 3 is a sectional view taken along line of FIG. 1 and shows steam-permeable portions and a gripper in an enlarged manner.

As shown in FIGS. 1, 2 and 3, the blood processing filter 1 according to the first embodiment has a square shape as a whole, and includes a sheet-shaped filter element 2 and a container 3. The container 3 includes an inlet-side container element 4 and an outlet-side container element 5 that are disposed to clamp the filter element 2 and adhere to each other. An internal space 3s is separated by the filter element 2 into an inlet space 4s and an outlet space 5s. The inlet-side container element 4 is provided with an inlet 4c that introduces the liquid to be processed into the inside. The outlet-side container element 5 is provided with an outlet 5c that discharges the liquid processed through the filter element 2. Although any of a rectangular shape, a disk shape, an elliptic shape and the like may be adopted as the blood processing filter 1, the rectangular shape is preferable to reduce the loss of material during production. A square shape and a rhombus are regarded as types of rectangular shapes.

(About Steam-Permeable Portion of Container According to First Embodiment)

At the container 3, steam-permeable portions 31 having steam permeability (characteristics of allowing steam to permeate) are formed. The formation of the steam-permeable portions 31 allows steam to enter the container 3 (inside of the blood processing filter 1) during execution of autoclave sterilization, and enables easy sterilization in the blood processing filter 1. An example of the steam-permeable portion 31 is described in detail.

Openings 32 are formed at about the centers of the inlet-side container element 4 and the outlet-side container element 5. The inlet-side container element 4 and the outlet-side container element 5 are each provided with a film 31a having steam permeability to block the openings 32. The film 31a having steam permeability (characteristics of allowing steam to permeate) is arranged at the inlet-side container element 4 or the outlet-side container element 5 to form the steam-permeable portion 31, which allows steam to enter the container 3 (inside of the blood processing filter 1) during execution of autoclave sterilization, and enables easy sterilization in the blood processing filter 1. In this embodiment, the mode has been described where the steam-permeable portion 31 is formed at both the inlet-side container element 4 and the outlet-side container element 5. Alternatively, a mode may be adopted where the steam-permeable portion 31 is formed at one of the inlet-side container element 4 and the outlet-side container element 5.

Examples of the material of the film 31a having steam permeability include polyvinyl chloride, hydrogenated styrene thermoplastic elastomer, polyolefin such as polyethylene and polypropylene, polyester such as polyethylene terephthalate, and resin such as polycarbonate, or the film may be a film 31a or the like usable for high pressure steam sterilization, such as Tyvek® made by pressing high-density polyethylene nonwoven fabric to achieve liquid-impermeability.

The gas permeable coefficient=the amount of gas permeation (volume)×thickness of steam-permeable portion (e.g., film 31a)/(pressure difference×permeation area×time). Accordingly, reduction in thickness of the steam-permeable portion 31 and increase in area can improve the steam permeability. Consequently, it is important to design the amount of gas (steam) permeation to be at least a certain amount (e.g., at least 0.50 g (measurement conditions: room temperature, 1 atm, and a day)) to achieve the thickness and area of the steam-permeable portion 31 that correspond to time during which autoclave sterilization is executed. An internal pressure occurs during filtration. Consequently, the strength for enduring the pressure is also required to be considered.

In this embodiment, ribs 4h and 5h are provided between the respective films 31a having steam permeability and the filter element 2. As a result, even if the internal pressure in the blood processing filter 1 becomes a negative pressure during filtration, the film 31a that allows steam to permeate is not pressed against the filter element 2. Consequently, it becomes unlikely to cause extension of filtering time and the like.

It is preferable that the wall thickness of another portion 31Y in the inlet-side container element 4 and the outlet-side container element 5 other than the film (steam-permeable portion) 31a range from 1 to 5 mm, inclusive. The configuration at least 1 mm achieves resistance to change in shape even when the internal pressure at the blood processing filter 1 in the outlet space 5s during filtration is a negative pressure. The configuration with the wall thickness of the other portion 31Y of the inlet-side container element 4 and the outlet-side container element 5 being 5 mm or less can prevent the molding time during container molding from increasing and prevent deformation due to insufficient cooling. The blood processing filter 1 according to this embodiment is provided with a film 31a serving as the steam-permeable portion for providing steam permeability, and secures the strength and rigidity which are of a filter, by configuring the thickness of the portion other than the steam-permeable portion to be at least a certain extent.

According to the method of forming the steam-permeable portion 31 at a part of any or both of the inlet-side container element 4 and the outlet-side container element 5 by providing the films 31a, the film 31a having steam permeability may be insertion-molded during molding of the container element through injection molding. Parts of the inlet-side container element 4 and the outlet-side container element 5 are hollowed. The film 31a may be caused to adhere thereon through a bonding method, such as of adhesives, high frequency or ultrasonic waves. In this case, insertion-molding is better because the insertion-molding can reduce steps. In the case where the materials of the inlet-side container element 4 and the outlet-side container element are materials that tend to allow steam to permeate, the steam-permeable portion 31 can be formed even without use of the film 31a. For example, in some cases, it is only required to form thin-walled portions to further improve the steam permeabilities of the inlet-side container element 4 and the outlet-side container element 5 themselves. In such cases, the thickness of the thin-walled portion may be a thickness ranging from 50 to 500 µm, inclusive, to improve the steam permeability.

Figure 4:
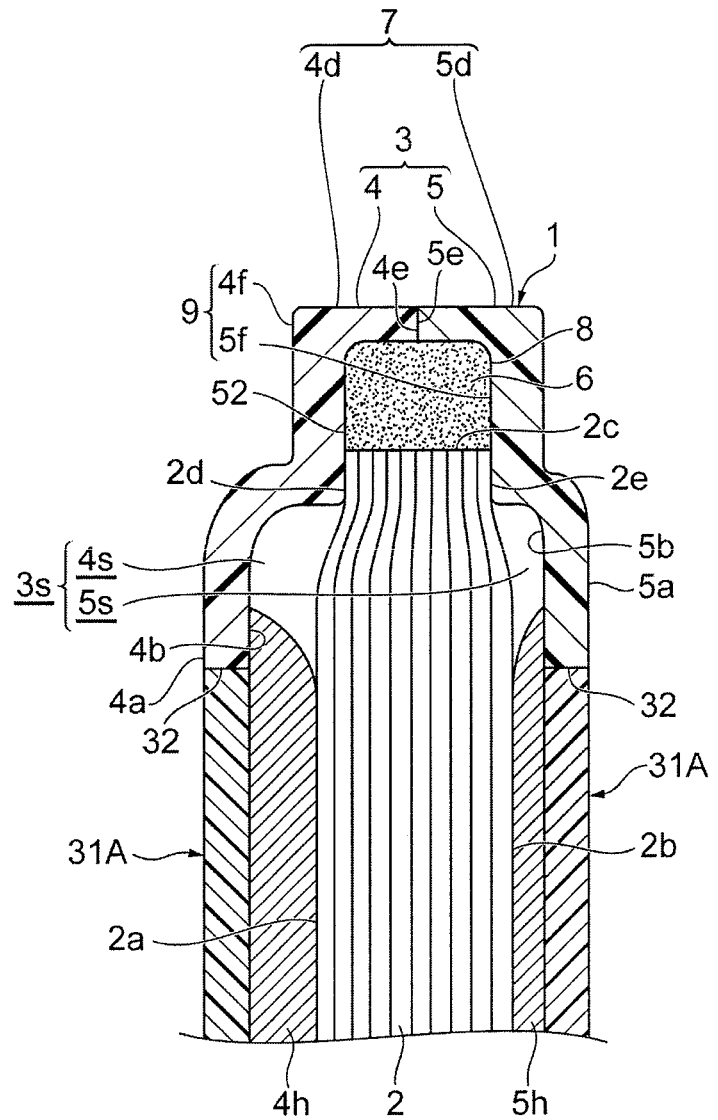
FIG. 4 corresponds to FIG. 3 and is a sectional view showing a variational example of steam-permeable portions according to the first embodiment in an enlarged manner.

As in a variational example of the steam-permeable portion 31, for example, as shown in FIG. 4, an opening 32 for autoclave sterilization may be formed at a part of one of or parts of both the inlet-side container element 4 and the outlet-side container element 5, a flexible resin having steam permeability may be provided to block the opening 32, thereby allowing a steam-permeable portion 31A to be formed.

(About Steam-Permeable Portion of Container According to Second Embodiment)

Figure 5:
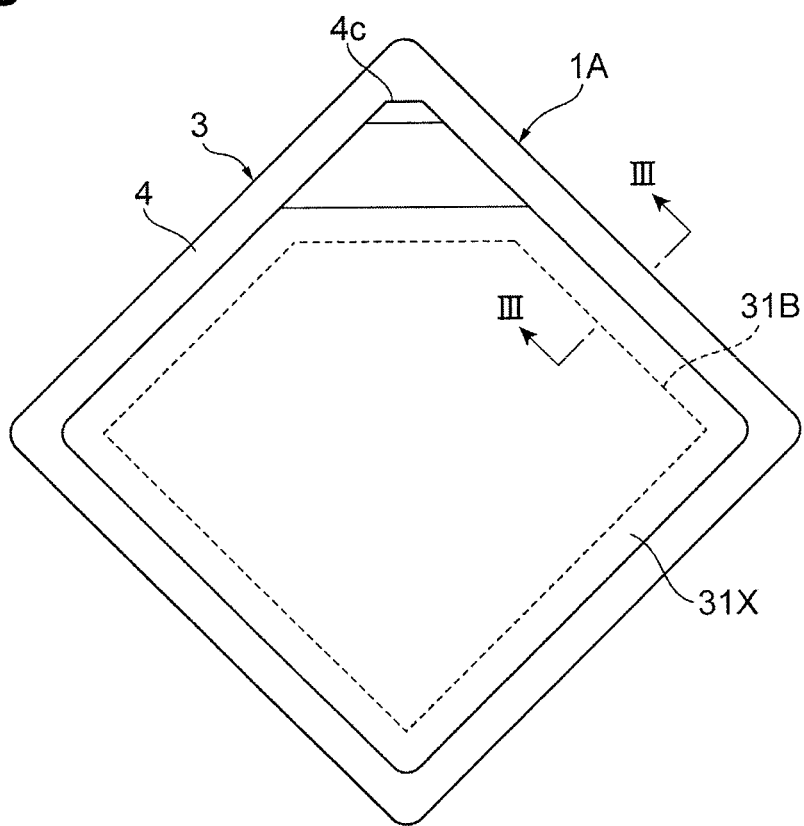
FIG. 5 is a plan view of a blood processing filter in view from the inlet-side container element according to a second embodiment of the present invention.
Figure 6:
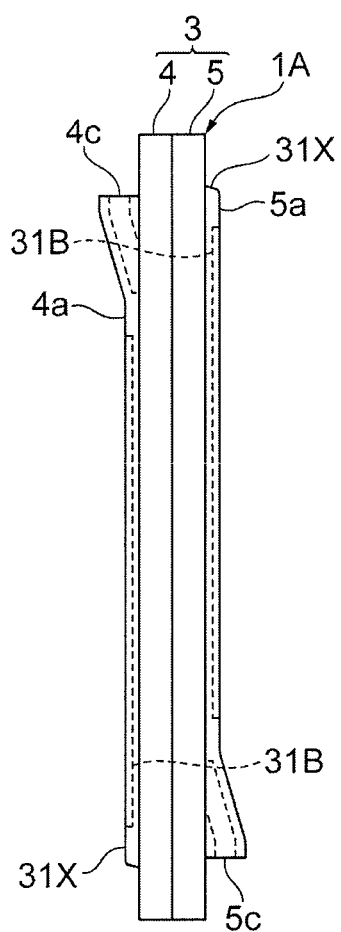
FIG. 6 is a side view of the blood processing filter according to the second embodiment of the present invention.
Figure 7:
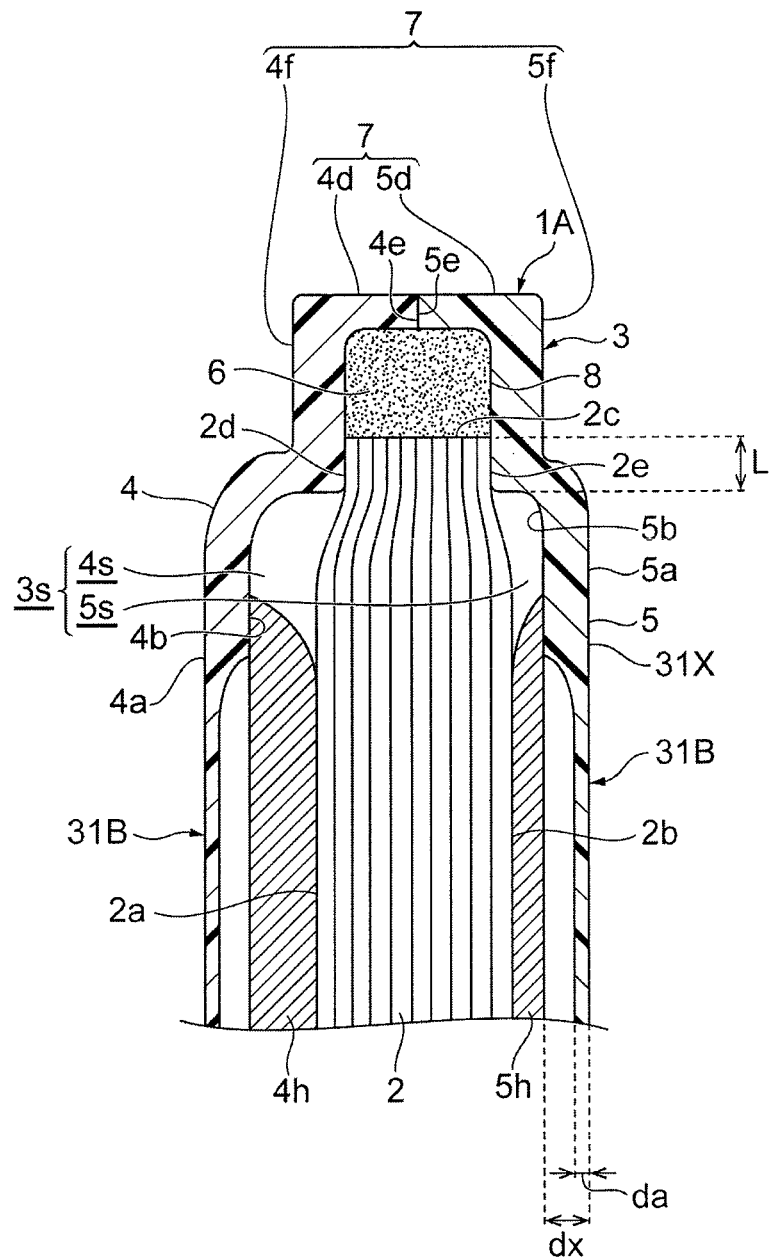
FIG. 7 is a sectional view taken along line 111411 of FIG. 5 and shows steam-permeable portions and a gripper in an enlarged manner.

As shown in FIGS. 5, 6 and 7, parts 31B of the inlet-side container element 4 and the outlet-side container element 5 according to the second embodiment are thin-walled portions that have smaller thickness (wall thickness) da than the thickness dx of another portion 31X. The thin-walled portion is integrally formed with the other portion (thick wall portion) 31X. Although there is some variation according to the materials of the inlet-side container element 4 or the outlet-side container element 5 where the thin-walled portion is formed, the thickness da of the thin-walled portion is configured to be small to an extent of having steam permeability (characteristics of allowing steam to permeate). As a result, the thin-walled portion serves as the steam-permeable portion 31B. More specifically, although there is some variation according to the materials of the inlet-side container element 4 and the outlet-side container element 5, it is preferable that the thickness da of the steam-permeable portion 31B range from 50 to 500 µm, inclusive. This is because in the case of 50 µm or less, the resin does not flow in during molding and difficulty in molding occurs, and in the case of exceeding 500 µm, the effect of steam permeability is reduced. The reduction in steam permeability means reduction to an extent of insufficient sterilization results. That is, the thickness da of the steam-permeable portion is required to be designed according to the container to be used and the object while ease with molding and advantageous effects of steam permeability are verified.

It is preferable that the wall thickness of the other portion 31X in the inlet-side container element 4 and the outlet-side container element 5 other than the steam-permeable portion 31B range from 1 to 5 mm, inclusive. The configuration at least 1 mm achieves resistance to change in shape even when the internal pressure at the blood processing filter 1A in the outlet space 5s during filtration is a negative pressure. The configuration with the wall thickness of the other portion 31X of the inlet-side container element 4 and the outlet-side container element 5 being 5 mm or less can prevent the molding time during container molding from increasing and prevent deformation due to insufficient cooling. The blood processing filter 1A according to this embodiment is provided with a steam-permeable portion 31B to provide steam permeability, and secures the strength and rigidity which are of a filter, by configuring the thickness of the portion other than the steam-permeable portion 31B to be at least a certain extent.

The following details are common to the blood processing filters 1 and 1A according to the first and second embodiments. Consequently, the blood processing filter 1 according to the first embodiment is typified and described.

(About Filter Element)

As shown in FIG. 3, the filter element 2 has a filtering surface 2a that faces the inlet space 4s, a filtering surface 2b that faces the outlet space 5s, and an end surface 2c along the peripheries of the pair of filtering surfaces 2a and 2b. The filter element 2 may be made of a filtering medium, such as a fibrous and porous medium, e.g., nonwoven fabric, woven fabric or the like, or a porous body having three-dimensional continuous reticulate pores, e.g., spongiform fabric. Note that what is other than a medium not excellent at adhesion, such as mesh or a screen, is preferable. Examples of the materials of the filter element 2 include polypropylene, polyethylene, styrene-isobutylene-styrene copolymer, polyurethane, polyester and the like. The case where the filter element 2 is made of nonwoven fabric is particularly preferable in view of productivity.

The filter element 2 may be a single filter element, or made of a plurality of filter elements made of stacked sheet-shaped filter materials. In the case where the element is made of a plurality of filter elements, it is preferable that the element include a first filter element that be disposed upstream and mainly remove microaggregates, and a second filter element that be disposed downstream of the first filter element for removing undesirable components other than microaggregates.

For example, a filter material made of nonwoven fabric having fiber diameters ranging from several to several tens of micrometers is disposed on the inlet side as the first filter element for mainly removing aggregates, a filter material made of nonwoven fabric having fiber diameters ranging from 0.3 to 3.0 vim is disposed as the second filter element for removing undesirable components other than aggregates, and these materials can be used. Each of the first and second filter elements may be made of a plurality of types of filter materials having different fiber diameters. Alternatively, only one of these elements may be made of a plurality of types of filter materials.

For example, a first titter element made of nonwoven fabric having fiber diameters ranging from 30 to 40 µm and/or nonwoven fabric having fiber diameters ranging from 10 to 20 µm may be disposed on the upstream side, and a second filter element made of nonwoven fabric having fiber diameters ranging from 1.5 to 2.5 µm and/or nonwoven fabric having fiber diameters ranging from 0.5 to 1.8 µm on the downstream side of the first filter element, thereby forming the filter element 2. Nonwoven fabric having large fiber diameters and nonwoven fabric having small fiber diameters may be alternately arranged. It is however preferable that the nonwoven fabric having large fiber diameters be arranged on the upstream side.

(About Gripper of Container) As described above, the container 3 is a square container having a predetermined thickness, and includes the inlet-side container element 4 and the outlet-side container element 5 which are arranged to clamp the filter element 2. The internal space 3s of the container 3 is separated by the filter element 2 into the inlet space 4s and the outlet space 5s. As described above, the filter element 2 has a filtering surface 2a that faces the inlet space 4s, a filtering surface 2b that faces the outlet space 5s, and an end surface 2c along the peripheries of the pair of filtering surfaces 2a and 2b.

The inlet-side container element 4 is a square member (see FIG. 2) that is a substantially half cut of the container 3 having substantially half the thickness, and includes an outer surface 4a, an inner surface 4b, and an end surface 4e along the peripheries of the outer surface 4a and the inner surface 4b. An inlet 4c is provided at the proximity of one corner of the outer surface 4a.

The outlet-side container element 5 is a square member that is the rest of the container 3, and includes an outer surface 5a, an inner surface 5b, and an end surface 5e along the peripheries of the outer surface 5a and the inner surface 5b. The outlet 5c is provided at a portion at an opposite corner opposite with respect to the corner provided with the inlet 4c, that is, close to the opposite corner. The inlet 4c and the outlet 5c are provided such that the inlet 4c opens upward, and the outlet 5c opens downward during use of the blood processing filter 1.

An outer edge portion including the end surfaces 4e and 5e of the inlet-side container element 4 and the outlet-side container element 5 is provided with an inlet-side contact portion 4d and an outlet-side contact portion 5d, respectively, which surround the end surface 2c of the filter element 2 and are brought into contact with each other to constitute a contact portion 7. In this embodiment, the end surfaces 4e and 5e are flat surfaces but may have female and male relationship to be fitted with each other.

The contact portion 7 is described further in detail. The outer edge portion of the inlet-side container element 4 is provided with the inlet-side contact portion 4d that has a shape oriented perpendicular to the plane along which portions other than the outer edge portion are disposed. A planer end surface 4e is provided at the distal end of the inlet-side contact portion 4d. Meanwhile, the outer edge portion of the outlet-side container element 5 is provided with the outlet-side contact portion 5d that has a shape oriented perpendicular to the plane along which portions other than the outer edge portion are disposed. A planer end surface 5e is provided at the distal end of the outlet-side contact portion 5d. As to the inlet-side container element 4 and the outlet-side container element 5, the end surface 4e of the inlet-side contact portion 4d (inlet-side container element 4) and the end surface 5e of the outlet-side contact portion 5d (outlet-side container element 5) face and are in contact with each other.

As shown in FIG. 3, the inside of the contact portion 7 is provided with a gripper 9 that clamps and compresses outer edge portions 2d and 2e of the pair of filtering surfaces 2a and 2b, which are the front and back of the filter element 2. The gripper 9 is formed of an inlet-side gripper 4f formed at the inlet-side container element 4, and an outlet-side gripper 5f formed at the outlet-side container element 5.

The inlet-side gripper 4f is made of a step that is the periphery of the inlet-side container element 4 curved toward the inner surface side (outlet-side container element 5 side) and bent to the outside. Likewise, the outlet-side gripper 5f is made of a step that is the periphery of the outlet-side container element 5 curved toward the inner surface side (inlet-side container element 4 side) and bent to the outside. The inlet-side gripper 4f and the outlet-side gripper 5f clamp and compress the outer edge portions 2d and 2e of the pair of filtering surfaces 2a and 2b that are the front and back of the filter element 2.

The gripper 9, which is formed of the inlet-side gripper 4f and the outlet-side gripper 5f, has a predetermined width at the outer edge portion of the container 3, and the portion nearer to the inside with respect to the width (inner portion) is used to hold the filter element 2. The portion nearer to the outside with respect to the width (outer portion) serves as a resin flow path 8 that surrounds the end surface 2c of the filter element 2 and is provided with the melt resin 6. The resin flow path 8 is a tubular (rectangular toroidal) cavity formed of the outer portion of the inlet-side gripper 4f, the outer portion of the outlet-side gripper 5f, the inlet-side contact portion 4d, the outlet-side contact portion 5d, and the end surface 2c of the filter element 2. The resin flow path 8 has a through-hole (not shown) that communicates with the outside of the container 3. The number of through-holes may be one or more. The resin flow path 8 is filled with the melt resin 6 through the through-hole, thereby allowing the filter element 2 to adhere to the end surface 2c, the inlet-side container element 4, and the outlet-side container element 5 with the melt resin 6 at the gripper 9. With such a belt-shaped adhesion of the inlet-side container element 4, the outlet-side container element 5, and the filter element 2 along the entire periphery of the gripper 9, the container 3 is sealed, which improves the airtightness and liquid-tightness.

The filter element 2 is not bonded at the gripper 9. This is because the method of adhesion between the filter element 2 and the container 3 is not based on heating bonding, such as ultrasonic bonding. Heating bonding melt a part of the filter element 2, and causes a portion integrally combined with the material of the container 3. However, this embodiment prevents occurrence of the portion integrally combined with the material of the container 3 through melting of a part of the filter element 2. This is because the method of adhesion between the filter element 2 and the container 3 is not based on the heating bonding such as ultrasonic bonding, and the filter element 2 is sufficiently compressed at the gripper 9 and the melt resin 6 injected into the resin flow path 8 do not enter the inside of the end surface 2c of the filter element 2. If the melt resin 6 enters the inside of the filter element 2 from the end surface 2c, the portion cannot maintain the function as the filter. However, in this embodiment, the filter element 2 maintains a function as a filter at portions other than the end surface 2c adhering to the melt resin 6, and is thus advantageous in blood processing efficiency.

Preferably, as to the function of the gripper 9, the filter element 2 is sufficiently compressed, which resultantly prevents the melt resin 6 injected into the resin flow path 8 from deforming the filter element 2 or entering the filter element 2. Thus, it is preferable to press the filter element 2 to have the density of that of the original resin. However, any structure can be adopted only if the structure is tolerable against the pressure of the melt resin 6 to be injected.

Figure 8:
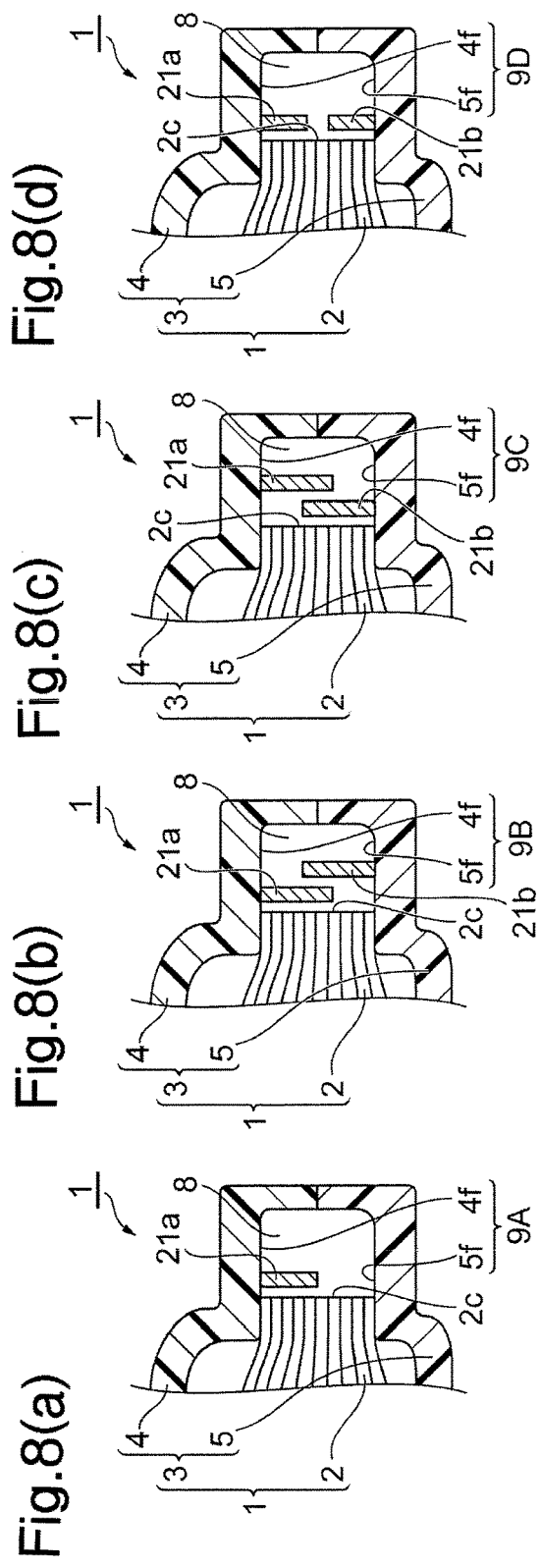
FIGS. 8(a)-8(d) are sectional views of variational examples where the grippers according to the first and second embodiments are provided with baffle plates.

For example, as shown in FIG. 8, a variational example of the gripper 9 may be grippers 9A, 9B, 9C and 9D formed by filling the resin flow path 8 having baffle plates 21a and 21b with the melt resin 6. More specifically, as shown in FIG. 8(a), a baffle plate 21a is provided for the inlet-side gripper 4f in parallel to the end surface 2c of the filter element 2. The baffle plate 21a is provided on the end surface 2c side with respect to the through-hole (not shown) of the resin flow path 8. The length of the baffle plate 21a is shorter than the thickness (the length in the compression direction) of the end surface 2c of the filter element 2.

As the gripper 9B shown in FIG. 8(b), a baffle plate 21b may also be provided at the outlet-side gripper 5f in parallel to the end surface 2c of the filter element 2 in a manner staggered with the baffle plate 21a. The baffle plates 21a and 21b are provided in an order of the baffle plates 21a and 21b from the end surface 2c. The lengths of the baffle plates 21a and 21b are smaller than the thickness of the end surface 2c of the filter element 2.

As with the gripper 9C shown in FIG. 8(c), baffle plates 21b and 21a may be provided in the order of the baffle plates 21b and 21a from the end surface 2c. For example, as with the gripper 9D shown in (d) of this diagram, the baffle plates 21a and 21b may be provided to have the same distance from the end surface 2c. In this case, the lengths of the baffle plates 21a and 21b are smaller than ½ of the thickness of the end surface 2c of the filter element 2.

As shown in FIG. 3, in an inner range surrounded by the inlet-side gripper 4f on the inner surface side of the inlet-side container element 4, a plurality of convex ribs 4h are provided. In an inner range surrounded by the outlet-side gripper 5f on the inner surface side of the outlet-side container element 5, a plurality of convexes 5h are provided. The ribs 4h of the inlet-side container element 4 are pressed against the filtering surface 2a of the filter element 2, and secure the inlet space 4s between the inner surface of the inlet-side container element 4 and the filtering surface 2a. Likewise, the ribs 5h of the outlet-side container element 5 are pressed against the filtering surface 2b of the filter element 2, and secure the outlet space 5s between the inner surface of the outlet-side container element 5 and the filtering surface 2b.

As described above, in the blood processing filter 1 according to this embodiment, the pair of filtering surfaces 2a and 2b of the filter element 2 is clamped by the ribs 4h and 5h, and partially compressed, thereby effectively and stably securing the inlet space 4s and the outlet space 5s. In this embodiment, the rib 4h of the inlet-side container element 4 has a larger height than the rib 5h. As a result, the inlet space 4s is secured larger than the outlet space 5s. The heights of the ribs 4h and 5h may be the same. On the contrary, the rib 5h may be higher.

(About Material of Container and Melt Resin)

The material of the container 3 (inlet-side container element 4 and outlet-side container element 5) and the melt resin 6 may be flexible material or hard material, for example, polycarbonate, polyester, polyamide, polystyrene, ABS, polyethylene, polypropylene, polyvinyl chloride, SBS, thermoplastic elastomer such as styrene-butadiene-styrene block copolymer, partially hydrogenated thermoplastic elastomer such as SBS, all types of thermoplastic resin such as perfectly hydrogenated styrene elastomer, thermosetting resin or the like.

In particular, in the case where the container including the inlet-side container element and the outlet-side container element is made of a flexible material, adhesion is typically made through heating bonding, such as high frequency bonding. However, in the case of heating bonding, the width of the adhesive portion is required to be increased for secure adhesion in order to maintain high leukocyte removing performance. There is a possibility of reduction in effective filtering area. On the other hand, this embodiment does not adopt heating bonding, and the end surface 2c adheres with the melt resin 6 instead. Even in the case where the container 3 is made of a flexible material, a high leukocyte removing performance can be secured while a wide effective filtering area is secured.

It is sufficient that materials that can easily adhere to each other are selected as the materials used for the container 3 and the melt resin 6. The materials may be different from or identical to each other. Typically, the case of the identical material is more conformable, thereby resultantly achieving easy adhesion between the filter element 2 and the container 3, which is preferable.

Any of resins with a high water vapor permeability including, for example, polystyrene resin, thermoplastic elastomer such as SBS, partially hydrogenated thermoplastic elastomer such as SBS, perfectly hydrogenated styrene elastomer, and flexible polyvinyl chloride is used as the material of the container 3, thereby allowing even the inside of the blood processing filter 1 to be sterilized by autoclave sterilization performed after the blood processing filter 1 is connected to the blood circuit. As to the material of the melt resin 6, as a resin with a lower melt viscosity is more conformable with the resin of the filter element 2, the adhesive strength between the end surface 2c of the filter element 2 and the melt resin 6 can be improved.

Next, methods for manufacturing the blood processing filters 1 and 1A according to the first and second embodiments are described. The methods for manufacturing the blood processing filters 1 and 1A according to the first and second embodiments are basically identical to each other. Consequently, the method for manufacturing the blood processing filter 1 according to the first embodiment is mainly described. As to the method for manufacturing the blood processing filter 1A according to the second embodiment, supplementary description is made on the difference.

An example of the method for manufacturing the blood processing filter 1 according to the first embodiment is described. The manufacturing method is described below using the blood processing filter 1 where the resin flow path 8 is formed at the contact portion 7 as an example. The blood processing filter 1 where the resin flow path 8 is not formed is basically according to analogous steps. First, an injection molding machine 10 used for the manufacturing method is described.

Figure 9:
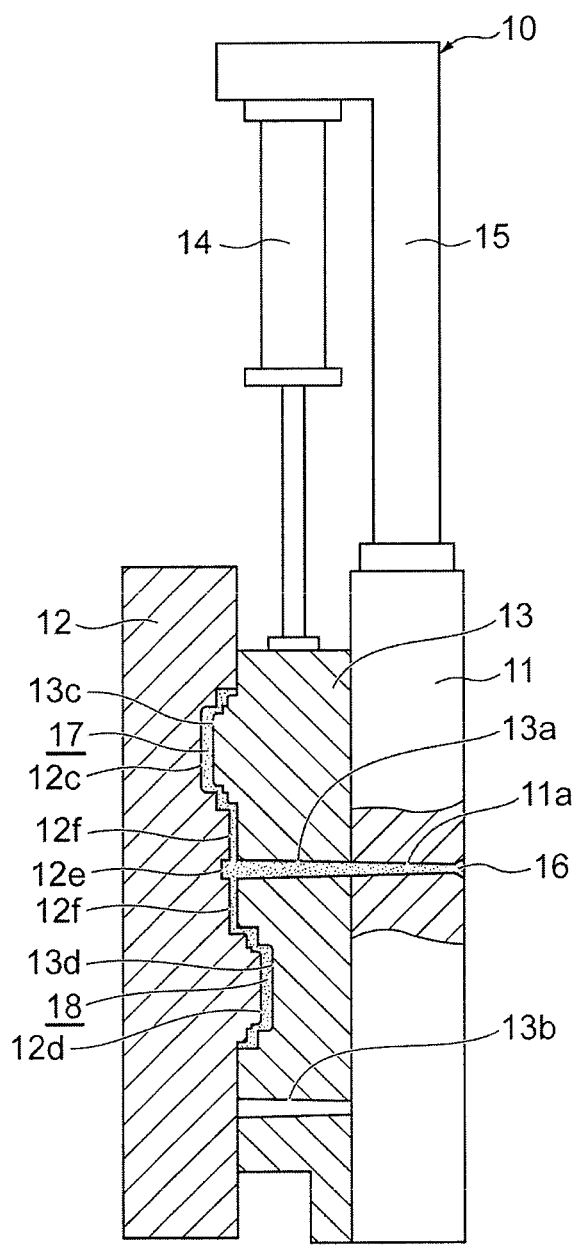
FIG. 9 is an illustration diagram for illustrating a container element molding step in manufacturing the blood processing filter according to the first and second embodiments.

As shown in FIG. 9, the injection molding machine 10 includes a fixed die 11, a movable die (mold) 12, and a slidable die (mold) 13. The fixed die 11 is fixed to a fixed platen (not shown) of the injection molding machine 10. A platform 15 that includes a cylinder 14 for sliding is provided on the upper surface of the fixed die 11. The cylinder 14 that is hydraulically or pneumatically moved is coupled onto the upper surface of the slidable die 13. The slidable die 13 is configured to be slidable and movable in a vertical direction while the state of being in close contact with a side surface of the fixed die 11 is kept.

The movable die 12 is attached to a movable platen (not shown) that is horizontally movable. The movable platen is configured to be movable in a manner close to but apart from the fixed die 11 by a mold opening and closing device (not shown) of the injection molding machine 10. The movable die 12 is configured to be movable between a mold fitting position of being in close contact with the slidable die 13, and a mold opening position of being apart from the slidable die 13.

The fixed die 11 is provided, at its center, with a sprue 11a for guiding melt resin 16 to be ejected from an injector (not shown) attached to the fixed die 11. The slidable die 13 is provided with a central sub-sprue 13a that continuously communicates with the sprue 11a when the die is at a lower position, and with a lower sub-sprue 13b that continuously communicates with the sprue 11a when the die is moved to an upper position.

Figure 10:
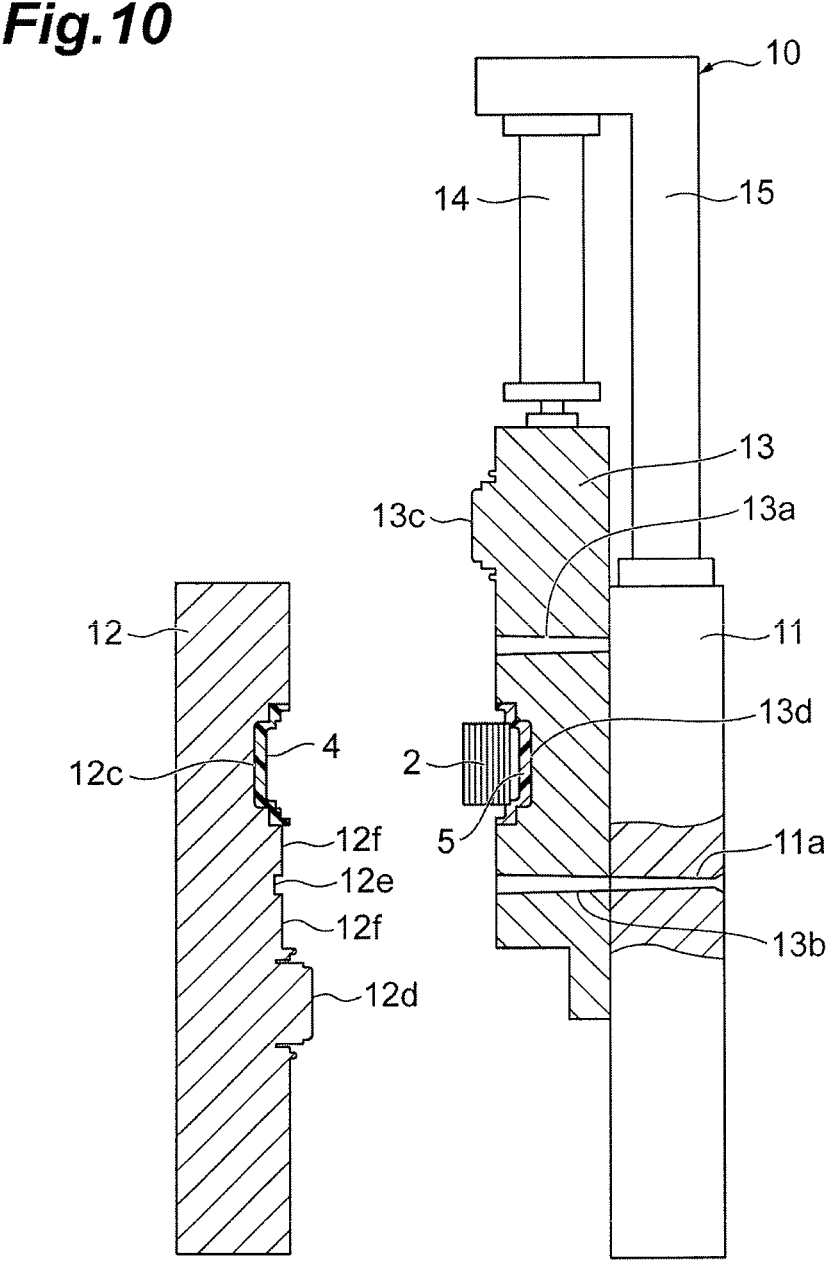
FIG. 10 is an illustration diagram for illustrating a inserting step in manufacturing the blood processing filter according to the first and second embodiments.
Figure 11:
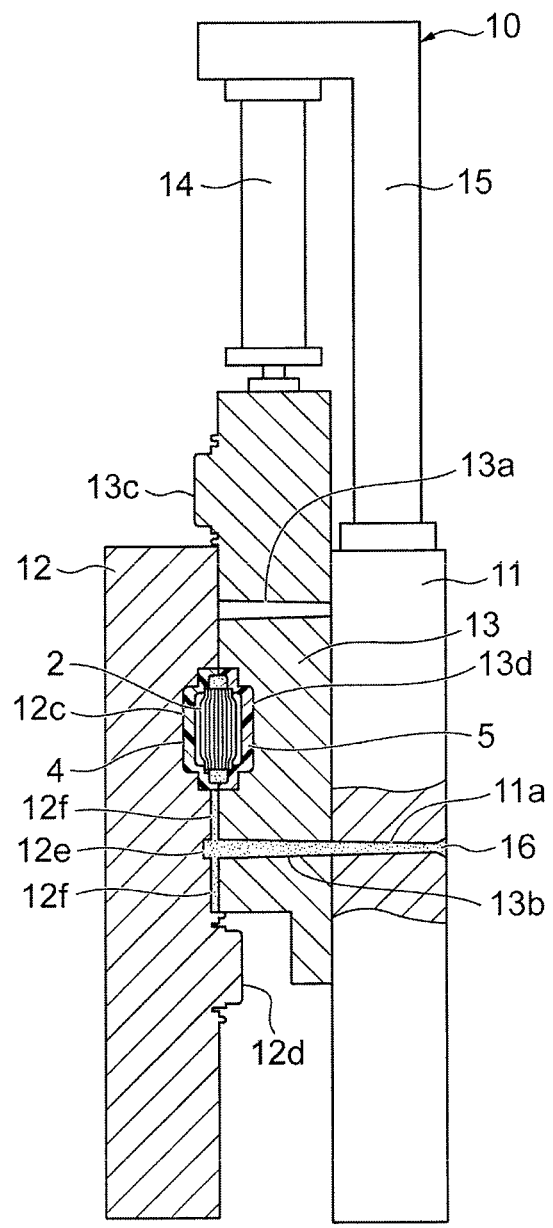
FIG. 11 is an illustration diagram for illustrating an adhesion step in manufacturing the blood processing filter according to the first and second embodiments.

A mold fitting surface of the slidable die 13 is provided with a male mold 13c and a female mold 13d at vertically symmetric positions with respect to the central sub-sprue 13a. The male mold 13c is for molding the inner surface 4b of the inlet-side container element 4, and the female mold 13d is for molding the outer surface 5a of the outlet-side container element 5. On the other hand, a mold fitting surface of the movable die 12 is provide with a female mold 12c and a male mold 12d facing the respective male mold 13c and female mold 13d when the slidable die 13 is at the lower position. The female mold 12c is for molding the outer surface 4a (see FIG. 3) of the inlet-side container element 4, and the male mold 12d is for molding the inner surface 5b of the outlet-side container element 5. As shown in FIGS. 10 and 11, the female mold 12c on the movable die 12 side is configured to face the female mold 13d on the slidable die 13 side when the slidable die 13 is at the upper position.

As shown in FIG. 9, when the slidable die 13 is at the lower position and the movable die 12 is mold-fitted therewith, a pair of gaps 17 and 18 surrounded by the male molds 12d and 13c and the female molds 13d and 12c are formed between the slidable die 13 and the movable die 12. At this time, the central sub-sprue 13a of the slidable die 13 is configured to communicate with these gaps through a runner 12e formed from the edge portions of the female molds 13d and 12c at the movable die 12 and through a pair of gates 12f. As shown in FIG. 11, when the slidable die 13 is at the upper position and the movable die 12 is mold-fit therewith, the female molds 13d and 12c of the slidable die 13 and the movable die 12 fit with each other, and the lower sub-sprue 13b and the runner 12e communicate with the edge portions of these female molds 13d and 12c through the gates 12f.

In order to mold the blood processing filter 1 using the injection molding machine 10, first, as shown in FIG. 9, the cylinder 14 is elongated to place the slidable die 13 at the lower position. Then, the movable platen of the injection molding machine 10 is moved on the fixed platen side, and mold-fits the slidable die 13 and the movable die 12. In this state, the central sub-sprue 13a of the slidable die 13 communicates with the sprue 11a of the fixed die 11, and the pair of gaps 17 and 18 are formed between the slidable die 13 and the movable die 12.

Next, the melt resin 16 is injected from the injector attached to the fixed platen, and the melt resin 16 is guided to both the gaps 17 and 18 through the sprue 11a of the fixed die 11, the central sub-sprue 13a of the slidable die 13, the runner 12e, and the gates 12f, and these gaps 17 and 18 are filled therewith. Thus, the pair of inlet-side container element 4 and outlet-side container element 5 are formed in the respective gaps 17 and 18 (container element molding step). At this time, the steam-permeable films 31a are preliminarily disposed in the mold and insertion molding is performed, which can fabricate the inlet-side container element 4 and the outlet-side container element 5 where the steam-permeable films 31a are disposed.

The method for manufacturing the blood processing filter 1A according to the second embodiment does not insertion-mold the film 31a in the container element molding step, and uses a mold that can form a portion of the container 3 which is a thin-walled portion thinner than the other portion 31X. This manufacturing method can fabricate the inlet-side container element 4 and the outlet-side container element 5 where the steam-permeable portion 31B which is a thin-walled portion having steam permeability is integrally formed with the other portion 31X.

After the inlet-side container element 4 and outlet-side container element 5 is cooled and solidified, the movable die 12 and the slidable die 13 are mold-opened by the mold opening and closing device and separated as shown in FIG. 10. Then, the male molds 13c and 12d are separated from the inlet-side container element 4 and the outlet-side container element 5, and the inlet-side container element 4 and the outlet-side container element 5 are left on the female molds 12c and 13s. In the mold opening, the resin portion solidified in the sprue 11a, the sub-sprue 13a, the runner 12e, the gates 12f and the like is pushed out of and dropped from the molds. The thus obtained inlet-side container element 4 and outlet-side container element 5 are provided with the inlet-side contact portion 4d and the outlet-side contact portion 5d, respectively, which are brought into contact with each other to form the contact portion 7, along the inner edge of the rectangular external shape.

Next, the filter element 2 made of polyester nonwoven fabric is inserted into the outlet-side container element 5, and subsequently the cylinder 14 is retracted to move the slidable die 13 to the upper position (inserting step). Then, the female mold 13d of the slidable die 13 and the female mold 12c of the movable die 12 face with each other, the inlet-side container element 4 and the outlet-side container element 5 left on the female molds 13d and 12c are brought into a state of facing each other. At this time, the lower sub-sprue 13b of the slidable die 13 is placed to communicate with the sprue 11a of the fixed die 11.

In this state, the movable die 12 is moved toward the slidable die 13, and these dies are brought into contact with each other and mold-fitted as shown in FIG. 11 (joining step). Then, the fitting surfaces of the inlet-side contact portion 4d and the outlet-side contact portion 5d are fitted with each other to form the contact portion 7. At the inside of the contact portion 7, the hollow resin flow path 8 is formed.

The resin flow path 8 has a through-hole, and communicates with the gates 12f through the through-hole. The gates 12f further communicate with the sub-sprue 13b through the runner 12e. In this state, the melt resin 16 serving as the melt resin 6, with which the resin flow path 8 is to be filled (see FIG. 11), is ejected from the injector. The melt resin 16 flows through the sprue 11a of the fixed die 11, the sub-sprue 13b, the runner 12e, the gates 12f, and the through-hole, and the resin flow path 8 is filled with this resin as the melt resin 6. Thus, the inlet-side container element 4 and the outlet-side container element 5 are caused to adhere to each other at the periphery of the contact portion 7 with the melt resin 6 (adhesion step). As described above, the method of filling with the melt resin 6 after formation of the resin flow path 8 achieves easy control of the amount of resin.

Adjust of the position of the through-hole in the case of injection of the melt resin 6 into the resin flow path 8 may allow the melt resin 6 to be injected in the direction perpendicular to the end surface 2c of the filter element 2, or allow the melt resin 6 to be injected in the direction horizontal to the end surface 2c. Preferably, to reduce the deformation of the filter element 2, it is desired that the pressure of injection not be applied to the filter element 2. Accordingly, a structure and the like where the baffle plates 21a and 21b (see FIG. 8) are arranged in the resin flow path 8 may be adopted.

The slidable die 13 and the movable die 12 are mold-opened after the melt resin 6 is cooled and solidified, and the inlet-side container element 4 and the outlet-side container element 5 are caused to adhere to each other, and thus the blood processing filter 1, which is finished as a completely sealed molded product, is obtained. The resin portions solidified in the sprue 11a, the sub-sprue 13b, the runner 12e, the gates 12f and the like are pushed out of and dropped from the molds.

After the thus completed blood processing filter 1 is taken out, the cylinder 14 is elongated again to place the slidable die 13 at the lower position. Then, the movable die 12 and the slidable die 13 are mold-fitted, and transition is made to a molding step for the next product. The series of steps as described above is repeated, thereby allowing the blood processing filters 1 to be successively molded. Furthermore, the simple molding step includes vertical sliding of the slidable die 13, mold-fitting and mold-opening through forward and backward movement of the movable die 12, and injection of the melt resin 16. Consequently, all the steps can be easily automated. Therefore, the blood processing filter 1 can be mass-produced.

Thus, only through use of the movable die 12 and the slidable die 13, which serve as the set of molds, and the injection molding machine 10, processes from injection molding of the inlet-side container element 4 and the outlet-side container element 5, and internal inserting of the filter element 2, and to bonding of the inlet-side container element 4 and the outlet-side container element 5, which are container elements, can be consecutively performed in a single step, and even what is completely sealed can be molded.

As described above, the blood processing filters 1 and 1A according to the first and second embodiments include: the sheet-shaped filter element 2; and the container 3 that includes the inlet-side container element 4 and outlet-side container element 5 disposed to clamp the filter element 2 and has the internal space 3s separated by the filter element 2 into the inlet space 4s and the outlet space 5s. The filter element 2 includes a pair of filtering surfaces 2a and 2b disposed on the inlet space 4s side and the outlet space 5s side, respectively. The inlet-side container element 4 and the outlet-side container element 5 are provided with the gripper 9 which clamps and compresses the outer edge portions 2d and 2e of the pair of filtering surfaces 2a and 2b and adheres to the end surface 2c with the melt resin 6. Parts of the container 3 are provided with steam-permeable portions 31, 31A and 31B having steam permeability. The steam-permeable portions 31 and 31A according to the first embodiment are made of a film 31a or a flexible resin. The steam-permeable portion 31B according to the second embodiment is a thin-walled portion which is thinner than the other portion 31X, and the steam-permeable portion 31 and the other portion 31X are integrally molded with each other.

The containers 3 for the blood processing filters 1 and 1A are thus provided with the steam-permeable portions 31, 31A and 31B having steam permeability. Consequently, sterilization in an autoclave can be easily executed. The inlet-side container element 4 and the outlet-side container element 5 are provided with the gripper 9 which clamps and compresses the outer edge portions 2d and 2e of the pair of filtering surfaces 2a and 2b. The gripper 9 is bonded to the end surface 2c along the periphery of the filtering surfaces 2*a* and 2*b* of the filter element 2 with melt resin 6. As a result, the side leakage (side flow) where undesirable components flow over the outer edge portions of the filter element 2 without being filtered is prevented, which is advantageous to improve blood processing efficiency. In particular, the gripper 9 is bonded to the end surface 2*c* of the filter element 2 with the melt resin 6. Consequently, the region of the outer edge portions 2*d* and 2*e* compressed by the gripper 9 to exert the advantageous effect can be reduced in comparison with a case without adhesion. As a result, the range of the filter element 2 that does not function for blood processing is reduced, which is preferable.

The filter element 2 is not bonded at the gripper 9 according to this embodiment. As a result, a portion where the function as the filter is lost decreases, which is further advantageous in improving the blood processing efficiency.

The gripper 9 has the resin flow path 8 which surround the end surface 2*c* of the filter element 2 and is filled with the melt resin 6. Consequently, the filter element 2 is loaded in the container 3, and subsequently the resin flow path 8 is filled with the melt resin, thereby allowing the end surface of the filter element to adhere through the resin flow path effectively.

Furthermore, the inlet-side container element 4, the outlet-side container element 5, and the filter element 2 adhere over the entire periphery of the gripper 9 in a belt-shaped manner by filling the resin flow path 8 with the melt resin 6. Consequently, the airtightness and liquid-tightness are high, which is preferable.

The method for manufacturing the blood processing filter 1 and 1A includes: a container element molding step of injection-molding the inlet-side container element 4 with one mold between the male mold 13*c* of the slidable die 13 and the female mold 12*c* of the movable die 12 and the outlet-side container element 5 with the other mold, and insert-molding the film 31*a* having steam permeability to form the steam-permeable portion 31; and a inserting step of inserting the filter element 2 into the inlet-side container element 4 or the outlet-side container element 5. In the blood processing filter 1A manufacturing method, the film 31*a* is not insertion-molded; alternatively, the thin-walled portion serving as the steam-permeable portion 31B is formed in the container element molding step.

Furthermore, the method includes: a joining step of mold-fitting the movable die 12 and the slidable die 13 which serve as a set of molds, of fitting the inlet-side container element 4 and the outlet-side container element 5 with each other, and of pressing the outer edge portions 2*d* and 2*e* of the filter element 2; and an adhesion step of causing the inlet-side container element 4 and the outlet-side container element 5 to adhere to each other with the melt resin 6.

This manufacturing method includes the joining step of fitting the inlet-side container element 4 and the outlet-side container element 5 with each other and applying a pressure to the elements, thereby allowing the inlet-side container element 4 and the outlet-side container element 5 to be pressed against each other by a strong power of, e.g., several tens of tf (ton-force). Ultrasonic bonding achieves approximately several hundreds of kgf (kilogram-force), and the inlet-side container element 4 and the outlet-side container element 5 can adhere to each other by ultrasonic bonding. Alternatively, according to this embodiment that executes the adhesion step after the joining step, the filter element 2 can be compressed to a high density.

The method for manufacturing the blood processing filter 1 and 1A according to this embodiment described above can effectively manufacture the aforementioned blood processing filters 1 and 1A.

Figure 12:
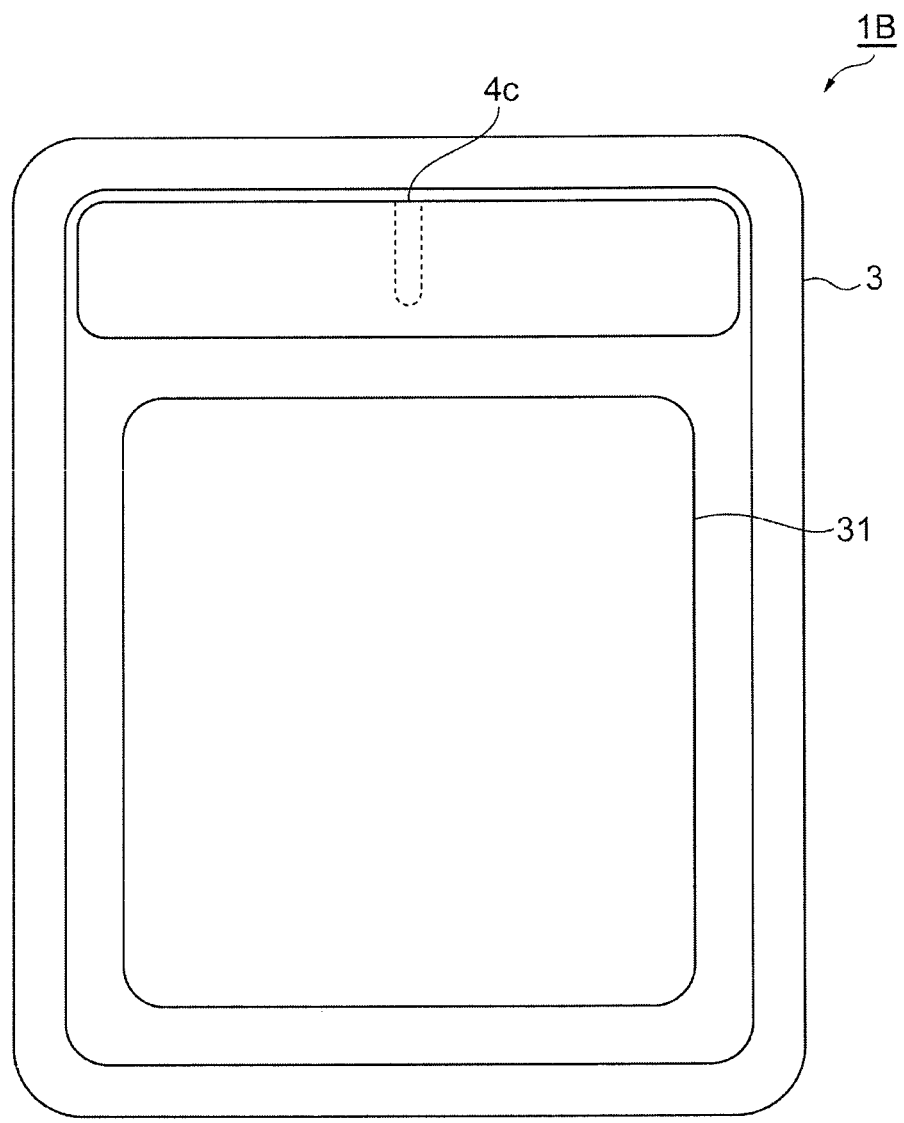
FIG. 12 is a plan view showing a blood processing filter according to another embodiment of the present invention, the filter being a rectangular blood processing filter.
Figure 13:
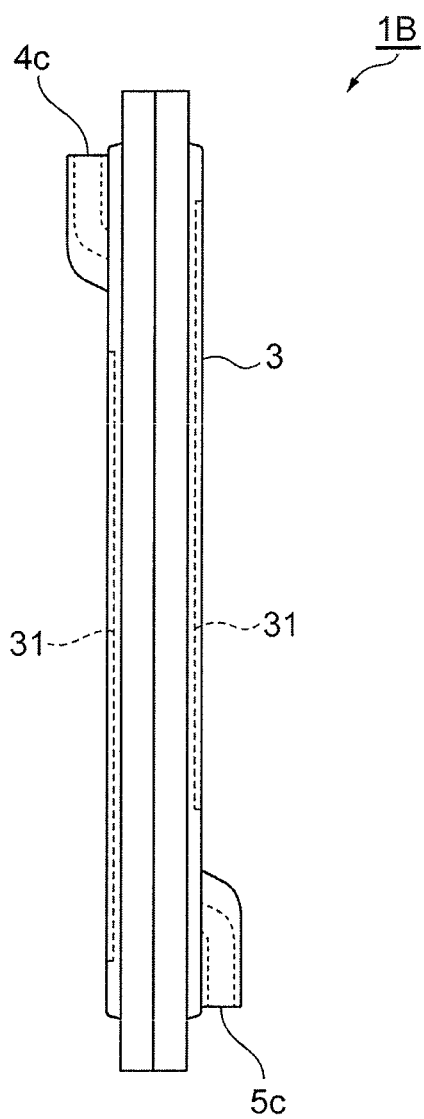
FIG. 13 corresponds to FIG. 12 and is a side view of the blood processing filter according to the other embodiment of the present invention.

Although the present invention has thus been described with reference to the embodiments, the present invention is not limited to the embodiments. For example, as shown in FIGS. 12 and 13, the blood processing filter 1B which has a rectangular shape as a whole may be adopted. In the case of the blood processing filter 1B according to the other embodiment, the filter element 2 (see FIG. 3) also has a rectangular shape in conformity with the rectangular container 3. The inlet-side container element 4 also has a rectangular shape. The inlet 4*c* is provided at the central portion on one short side of the inlet-side container element 4 to open on one side. The outlet-side container element 5 also has a rectangular shape. The outlet 5*c* is provided at the central portion on the other short side of the outlet-side container element 5 to open on the other side.

In adhesion between the inlet-side container element and the outlet-side container element according to the present invention, heating bonding such as ultrasonic bonding may be partially utilized. That is, the inlet-side container element and the outlet-side container element may be bonded with ultrasonic bonding, subsequently, the resin flow path may be filled with the melt resin, and the filter element 2 and the container may be caused to adhere to each other with melt resin. As described above, to prevent the melt resin injected into the inside of the resin flow path from deforming the filter element or entering the inside of the filter element from the end surface, the filter element is required to be sufficiently compressed by the gripper.

Note that, in the case of ultrasonic bonding typically used for container adhesion, it is difficult to compress the filter element to a high density. Even in the compressible case, leakage at a bonded portion of the bonded blood processing filter occurs, and a crack or the like occurs due to excessive pressing of the containers to each other, which are problems in yield. Consequently, even in the case of ultrasonic bonding, adhesion with melt resin is necessary.

EXAMPLES

The present invention will now be described in further detail below by way of examples. However, the present invention is not limited to these examples.

(Filtering Performance Evaluation on Whole Blood)

A whole blood preparation adjusted as follows was used for filtering performance evaluation. 2100 mL of pig whole blood was collected and mixed into a blood bag containing 320 mL of anticoagulant CPD, and relatively coarse aggregates generated during blood collection were removed by filtration with a preprocess filter other than the blood processing filters of Examples and Comparative Examples of blood processing filters, which will be described later. The preprocess filter has a configuration where twelve sheets with an average value of pore diameters of 60 μm and a weight per unit area of 50 g/m$^2$, eight sheets with an average value of pore diameters of 50 μm and a weight per unit area of g/m$^2$, and eight sheets with an average value of pore diameters of 50 μm and a weight per unit area of 30 g/m$^2$ are stacked from the upstream side in this order, and accommodated in a container made of a hard resin with a filtering area of 45 cm$^2$. The blood from which the coarse aggregates in blood collection had been removed by the preprocess filter during blood collection was divided into 460 mL-portions and injected into respective bags on the day of blood collection. The thus obtained whole blood preparations were left at room temperature, and filtered with the blood filters of Examples and Comparative Examples at room temperature on the day of the blood collection. The filtering time from the start to the end of filtration was measured, and regarded as the filtering time. The leukocyte removing performance was calculated by the following Equation (1).

Leukocyte removing performance=Log (concentration of leukocyte before filtering (cells/µL)/concentration of leukocyte after filtration (cells/µL))     (1)

The concentrations of leukocyte before and after filtering were measured using an automatic blood cell analyzer SF3000 (Sysmex Corporation).

(Autoclave Sterilization Performance Evaluation)

What includes a blood filter and a bioindicator inserted therein was fabricated, and stoppers made of PVC were used for the inlet of the inlet-side container element and the outlet of the outlet-side container element, thereby preventing steam from entering through the inlet or the outlet during sterilization. The sterilization was executed at 123° C. for 30 minutes, and the performance of sterilization was evaluated according to presence or absence of cultured bacteria.

Example 1

The blood processing filter according to Example 1 was fabricated using the method for manufacturing the blood processing filter 1 according to the aforementioned embodiment. That is, the inlet-side container element was formed by the one mold and the outlet-side container element was formed by the other mold, and subsequently the blood processing filter element was loaded into the outlet-side container element, and the inlet-side container element and outlet-side container element were brought into contact with each other by moving the mold. Subsequently, the blood processing filter was fabricated using the method of injecting the melt resin through the flow path of the mold formed at the periphery of the contact portion of the inlet-side container element and the outlet-side container element into the resin flow path of the container and of bonding the entire periphery of the fitting portion.

The material of the melt resin with which the container and the melt resin flow path was filled, or which was injected into the path, was polycarbonate resin, and the distance of the gripper, i.e., the distance between the surfaces of the inlet-side gripper and the outlet-side gripper which face with each other was 2.0 mm. The outer edge portions of the front and back filtering surfaces of the filter element were configured such that the compression region clamped and compressed by the inlet-side gripper and the outlet-side gripper was a region having a distance range of 5 mm from the end surface of the filter element toward the inside. At this time, the effective filtering area was configured to 46 cm². A film (having steam permeability) that allows steam to pass was provided to have an area of 13 cm² for the inlet-side container. A film having steam permeability was provided to have an area of 16 cm² for the outlet-side container element. The steam-permeable portion was created for each. Here, a film made of polyvinyl chloride having a thickness of 0.2 mm was used as a film having steam permeability. The original thickness D0 of the filter element was 9 mm. The compressibility ratio by the gripper was 22.2%. Furthermore, polyester nonwoven fabric was stacked according to the following configuration for use as the filter element.

Polyester nonwoven fabric 1 (the average fiber diameter was 12 µm, and the weight per unit area was 30 g/m²) 6 sheets
Polyester nonwoven fabric 2 (the average fiber diameter was 1.6 µm, and the weight per unit area was 66 g/m²) 2 sheets
Polyester nonwoven fabric 3 (the average fiber diameter was 1.2 µm, and the weight per unit area was 30 g/m²) 32 sheets The result of an experiment through use of the thus created blood processing filter is shown in Table 1. The leukocyte removing performance was 1.52, which showed high performance. Live bacteria after sterilization were not identified.

Example 2

Hydrogenated styrene thermoplastic elastomer was adopted as the container material. A film having steam permeability was provided to have an area of 13 cm² for the inlet-side container element. A film having steam permeability was provided to have an area of 16 cm² for the outlet-side container element. The steam-permeable portion was created for each. Here, a film made of polycarbonate having a thickness of 0.1 mm was used as a film having steam permeability. Note that the blood processing filter was fabricated as with Example 1 except for the aforementioned conditions. The result of an experiment through use of the thus fabricated blood processing filter is shown in Table 1. The leukocyte removing performance is 1.45, which showed high performance. Live bacteria after sterilization were not identified.

Example 3

Hydrogenated styrene thermoplastic elastomer was adopted as the container material. No film having steam permeability was provided for the inlet-side container element. A film having steam permeability was provided to have an area of 16 cm² only for the outlet-side container element, and the steam-permeable portion was created. The blood processing filter was fabricated in a manner analogous to that in Example 1 except that a film made of flexible polyvinyl chloride having a thickness of 0.1 mm was used as a steam-permeable film. The result of an experiment through use of the thus fabricated blood processing filter is shown in Table 1. As a result of execution of an experiment through use of this blood processing filter, the leukocyte removing performance was 1.46, which showed a high performance. Live bacteria after sterilization were not identified.

Comparative Example 1

The inlet-side container element was formed by the one mold and the outlet-side container element was formed by the other mold, and subsequently the inlet-side container element and the outlet-side container element were taken out, and the filter element was loaded. The blood processing filter was fabricated such that the inlet-side contact portion and the outlet-side contact portion were caused to adhere to each other but the end surface of the filter element was not caused to adhere. Furthermore, the blood processing filter was fabricated in a manner analogous to that in Example 1 except that polycarbonate was adopted as the container material and no film having steam permeability was disposed. The result of an experiment through use of the blood processing filter of this Comparative Example is shown in Table 1. As a result of execution of an examination using this blood processing filter, the leukocyte removing performance was 0.28, which showed a much lower performance than that in each Example. Live bacteria after sterilization were identified.

Comparative Example 2

The inlet-side container element was formed by the one mold and the outlet-side container element was formed by the other mold, and subsequently the inlet-side container element and the outlet-side container element were taken out, and the filter element was loaded. The blood processing filter was fabricated in a manner analogous to that of Example 1 except that the inlet-side contact portion and the outlet-side contact portion were caused to adhere to each other, but the end surface of the filter element was not caused to adhere. Note that in Comparative Example 2, steam-permeable portions analogous to those in Example 1 were formed at the inlet-side contact portion and the outlet-side contact portion. The result of an experiment through use of this blood processing filter of this Comparative Example is shown in Table 1. As a result of execution of an examination using this blood processing filter, the leukocyte removing performance was 0.25, which showed a much lower performance than that in each Example. However, live bacteria after sterilization were not identified.

Comparative Example 3

The blood processing filter was fabricated in a manner analogous to that in Example 1 except that polycarbonate was adopted as the container material and no steam-permeability film was formed. Note that in Comparative Example 3, the inlet-side contact portion and outlet-side contact portion were caused to adhere to the end surface of the filter element with melt resin. The result of an experiment through use of this blood processing filter of this Comparative Example is shown in Table 1. As a result of execution of an experiment through use of this blood processing filter, the leukocyte removing performance was 1.49, which showed a high performance. However, live bacteria after sterilization were identified.

TABLE 1

| | Leukocyte removing capability (−) | Sterilization |
|---|---|---|
| Example 1 | 1.52 | Good |
| Example 2 | 1.45 | Good |
| Example 3 | 1.46 | Good |
| Comparative example 1 | 0.28 | Not good |
| Comparative example 2 | 0.25 | Good |
| Comparative example 3 | 1.49 | Not good |

Example 4

The material of the melt resin with which the container and the melt resin flow path was filled, or which was injected into the path, was polycarbonate resin, and the distance of the gripper, i.e., the distance between the surfaces of the inlet-side gripper and the outlet-side gripper which face with each other was 2.0 mm. The outer edge portions of the front and back filtering surfaces of the filter element were configured such that the compression region clamped and compressed by the inlet-side gripper and the outlet-side gripper was a region having a distance range of 5 mm from the end surface of the filter element toward the inside. At this time, the effective filtering area was configured to 46 cm$^2$. A thin-walled portion (having steam permeability) that allows steam to pass was provided to have an area of 13 cm$^2$ for the inlet-side container. A thin-wailed portion having steam permeability was provided to have an area of 16 cm$^2$ for the outlet-side container element. A steam-permeable portion was created for each. Here, the thickness of the thin-walled portion as the steam-permeable portion was configured to be 0.2 mm. The original thickness DO of the filter element was 9 mm. The compressibility ratio by the gripper was 22.2%. Furthermore, polyester nonwoven fabric was stacked according to the following configuration for use as the filter element.

Polyester nonwoven fabric 1 (the average fiber diameter was 12 μm, and the weight per unit area was 30 g/m$^2$) 6 sheets
Polyester nonwoven fabric 2 (the average fiber diameter was 1.6 μm, and the weight per unit area was 66 g/m$^2$) 2 sheets
Polyester nonwoven fabric 3 (the average fiber diameter was 1.2 μm, and the weight per unit area was 30 g/m$^2$) 32 sheets
The result of an experiment through use of the thus fabricated blood processing filter is shown in Table 2. The leukocyte removing performance is 1.55, which showed high performance. Live bacteria after sterilization were not identified.

Example 5

The blood processing filter was fabricated in a manner analogous to that in Example 4 except that hydrogenated styrene thermoplastic elastomer was adopted as the container material. The result of an experiment through use of the thus fabricated blood processing filter is shown in Table 2. The leukocyte removing performance is 1.48, which showed high performance. Live bacteria after sterilization were not identified.

Example 6

The blood processing filter was fabricated in a manner analogous to that in Example 4 except that hydrogenated styrene thermoplastic elastomer was adopted as the container material, no thin-walled portion was formed at the inlet-side container element, and the thin-walled portion (thickness of 0.1 mm) was formed to have an area of 16 cm$^2$ only at the outlet-side container element. The result of an experiment through use of the thus fabricated blood processing filter is shown in Table 2. As a result of execution of an experiment through use of this blood processing filter, the leukocyte removing performance was 1.56, which showed a high performance. Live bacteria after sterilization were not identified.

Comparative Example 4

The inlet-side container element was formed by the one mold and the outlet-side container element was formed by the other mold, and subsequently the inlet-side container element and the outlet-side container element were taken out, and the filter element was loaded. The blood processing filter was fabricated such that the inlet-side contact portion and the outlet-side contact portion were caused to adhere to each other but the end surface of the filter element was not caused to adhere. The blood processing filter was fabricated in a manner analogous to that in Example 4 except that polycarbonate was adopted as the container material and no thin-walled portion was formed. The result of an experiment through use of this blood processing filter of this Comparative Example is shown in Table 2. As a result of execution of an examination using this blood processing filter, the leukocyte removing performance was 0.28, which showed a much lower performance than that in each Example. Live bacteria after sterilization were identified.

Comparative Example 5

The inlet-side container element was formed by the one mold and the outlet-side container element was formed by the other mold, and subsequently the inlet-side container element and the outlet-side container element were taken out, and the filter element was loaded. The blood processing filter was fabricated in a manner analogous to that of Example 4 except that the inlet-side contact portion and the outlet-side contact portion were caused to adhere to each other but the end surface of the filter element was not caused to adhere. Note that in Comparative Example 5, steam-permeable portions analogous to those in Example 4 were formed at the inlet-side contact portion and the outlet-side contact portion. The result of an experiment through use of this blood processing filter of this Comparative Example is shown in Table 2. As a result of execution of an examination using this blood processing filter, the leukocyte removing performance was 0.3, which showed a much lower performance than that in each Example. Meanwhile, live bacteria after sterilization were not identified.

Comparative Example 6

The blood processing filter was fabricated in a manner analogous to that in Example 4 except that no thin-walled portion was formed. As a result of execution of an experiment through use of this blood processing filter, the leukocyte removing performance was 1.49, which showed a high performance. However, live bacteria after sterilization were identified.

TABLE 2

|  | Leukocyte removing capability (–) | Sterilization |
| --- | --- | --- |
| Example 4 | 1.55 | Good |
| Example 5 | 1.48 | Good |
| Example 6 | 1.56 | Good |
| Comparative example 4 | 0.28 | Not good |
| Comparative example 5 | 0.3 | Good |
| Comparative example 6 | 1.49 | Not good |

REFERENCE SIGNS LIST 1, 1A, 1B . . . Blood processing filter, 2 . . . Filter element, 2a, 2b . . . Filtering surface, 2c . . . End surface, 2d, 2e . . . Outer edge portion, 3 . . . Container, 3s . . . Internal space, 4 . . . Inlet-side container element, 4s . . . Inlet space, 5 . . . Outlet-side container element, 5s . . . Outlet space, 6 . . . Melt resin, 8 . . . Resin flow path, 9, 9A, 9B, 9C, 9D . . . Gripper, 12 . . . Movable die (one mold), 3 . . . Slidable die (other mold), 31, 31A . . . Steam-permeable portion, 31X, 31Y . . . Other portion, 31a . . . Film, 31B . . . Steam-permeable portion, dx . . . Thickness of steam-permeable portion, da . . . Thickness of other portion.

The invention claimed is:

1. A blood processing filter for removing undesirable components from liquid containing a blood component or blood, the filter comprising:
   a sheet-shaped filter element; and
   a container that includes an inlet-side container element and an outlet-side container element that are disposed to clamp the filter element, and has an internal space separated by the filter element into an inlet space and an outlet space,
   wherein the filter element includes a pair of filtering surfaces disposed on the inlet space side and the outlet space side, and an end surface along peripheries of the pair of filtering surfaces,
   the inlet-side container element and the outlet-side container element are provided with a gripper that clamps and compresses outer edge portions of the pair of filtering surfaces and adheres to the end surface with melt resin, and
   the container having a steam-permeable portion and other portion provided at a periphery of the steam-permeable portion, the steam-permeable portion and the other portion being made of a hard material and integrally formed with each other, and the steam-permeable portion being thinner than the other portion, and
   wherein the hard material is configured to inhibit deformation of the container during filtration.

2. The blood processing filter according to claim 1, wherein the steam-permeable portion has a thickness of 50 µm or more and 500 µm or less.

3. The blood processing filter according to claim 1, wherein a portion of the filter element where the gripper clamps and compresses is not injected with the melt resin.

4. The blood processing filter according to claim 1, wherein the melt resin is made of a material identical to that of the container.

5. The blood processing filter according to claim 1, wherein the gripper further includes a resin flow path that surrounds the end surface of the filter element and is filled with the melt resin.

6. The blood processing filter according to claim 5, wherein the inlet-side container element, the outlet-side container element, and the filter element adhere over an entire periphery of the gripper in a belt-shaped manner by the resin flow path being filled with the melt resin.

7. The blood processing filter according to claim 2, wherein the other portion of the container has a thickness of 1 mm or more and 5 mm or less.

8. The blood processing filter according to claim 1, wherein the end surface of the filter element provides an outermost end surface of the outer edge portions and is clamped and compressed by the gripper.

9. The blood processing filter according to claim 1, wherein the hard material is selected from a group consisting of: polycarbonate and acrylonitrile butadiene styrene.

* * * * *